US008947668B2

(12) United States Patent
Hulme et al.

(10) Patent No.: US 8,947,668 B2
(45) Date of Patent: Feb. 3, 2015

(54) METHOD FOR DETERMINING THE PATH LENGTH OF A SAMPLE AND VALIDATING THE MEASUREMENT OBTAINED

(75) Inventors: A Keith Hulme, Essex (GB); John Hammond, Essex (GB); Nathan Hulme, Essex (GB)

(73) Assignee: Starna Scientific Limited (GB)

( * ) Notice: Subject to any disclaimer, the term of this patent is extended or adjusted under 35 U.S.C. 154(b) by 49 days.

(21) Appl. No.: 13/617,478

(22) Filed: Sep. 14, 2012

(65) Prior Publication Data

US 2013/0070236 A1    Mar. 21, 2013

(30) Foreign Application Priority Data

Sep. 16, 2011    (GB) .................................. 1116080.1

(51) Int. Cl.
*G01N 21/00*    (2006.01)
*G01N 21/11*    (2006.01)
*G01N 21/27*    (2006.01)

(52) U.S. Cl.
CPC .............. *G01N 21/11* (2013.01); *G01N 21/274* (2013.01); *G01N 21/278* (2013.01); *G01N 2201/0662* (2013.01); *G01N 2201/1286* (2013.01)
USPC ......................................................... 356/432

(58) Field of Classification Search
CPC .................................................. G01N 21/1702
USPC ......................................................... 356/432
See application file for complete search history.

(56) References Cited

U.S. PATENT DOCUMENTS

| 4,939,095 | A | 7/1990 | Yokotani |
| 5,959,738 | A | 9/1999 | Hafeman et al. |
| 6,188,476 | B1 | 2/2001 | Hafeman et al. |
| 6,320,662 | B1 | 11/2001 | Hafeman et al. |
| 6,339,472 | B1 | 1/2002 | Hafeman et al. |
| 6,404,501 | B1 | 6/2002 | Hafeman et al. |
| 7,791,716 | B2 * | 9/2010 | McNally et al. ............... 356/36 |
| 7,847,944 | B2 * | 12/2010 | Buettner et al. ............. 356/436 |
| 2005/0168737 | A1 | 8/2005 | Bradshaw et al. |

FOREIGN PATENT DOCUMENTS

| WO | 9603637 A1 | 2/1996 |
| WO | 2007131945 A2 | 11/2007 |

OTHER PUBLICATIONS

Intellectual Property Office, Search Report under Section 17 issued in priority application No. GB1116080.1, Nov. 22, 2012.

\* cited by examiner

*Primary Examiner* — Tarifur Chowdhury
*Assistant Examiner* — Md Rahman
(74) *Attorney, Agent, or Firm* — Stites & Harbison, PLLC; David W. Nagle, Jr.; Stephen J. Weyer

(57) ABSTRACT

A for traceably determining an unknown optical path length of a sample in an optical measuring device comprises the steps of: providing a drop analyzer connected to a standard spectrophotometer; providing a certified reference material contained in first and second closed high accuracy cuvettes; measuring absorbance of the certified reference material to obtain a first absorbance measurement for the first specified path length; measuring absorbance of the certified reference material for a second path length to obtain a second absorbance measurement; using a dropping device to drop a specified volume of the solvent on an optical surface so that the path length of the specified volume can be determined by reference to the first and second absorbance measurement; and using the dropping device to drop the same volume of sample as the specified volume of solvent on the optical measuring device.

9 Claims, 2 Drawing Sheets

METHOD FOR DETERMINING THE PATH LENGTH OF A SAMPLE AND VALIDATING THE MEASUREMENT OBTAINED

CROSS-REFERENCE TO RELATED APPLICATIONS

The present application claims priority to GB Application No. 1116080.1 filed on Sep. 16, 2011.

BACKGROUND OF THE INVENTION

The present invention relates to a method for determining an unknown optical path length and for validating the measurement obtained, in particular a traceable method for determining the path length of a volume such as a drop.

Metrology is a science which is concerned with measurement; specifically, it includes experimental and theoretical determinations in any field of technology. The international vocabulary of metrology is maintained by the International Organisation for Standardisation (ISO) and is currently in its third revision.

One of the core bases of metrology is metrological traceability, which is defined as the property of the result of a measurement or the value of a standard whereby it can be related to references, usually national or international standards, through an unbroken chain of comparisons all having stated uncertainties. In many countries, national standards for weights and measures are maintained by a National Metrology Institute (NMI) which provides the highest level of standards for the calibration or measurement traceability infrastructure in that country. For example, In the UK, the NMI is the National Physical Laboratory (NPL), in the US the NMI is called National Institute of Standards and Technology (NIST), in Germany the NMI is the Physikalisch-Technische Bundesanstalt (PTB) and in Canada the NMI is the NRC Institute for National Measurement Standards (NRC).

Typically, traceability is achieved by calibration which establishes the relation between the result shown in a measuring instrument and the value of a measured standard. Thus, calibration to a traceable standard can be used to determine whether an instrument is precise and accurate and it can also be used to determine whether the instrument has a bias.

Traceability can also be obtained from a derived unit back to one of the fundamental units of the International System of Units (SI) convention. In the present invention, a derived unit, specifically absorbance, is traced back to the metre.

The Beer-Lambert law states that there is a logarithmic dependence between the transmission or transmissivity (T) of light through a substance and the product of the absorption coefficient (α) of the same substance and the distance the light travels through the material, commonly referred to as the path length (l). Accordingly, the absorption coefficient (α) can be expressed as a product of either: (a) the extinction coefficient or molar absorptivity of the substance (ε) and the concentration (c) of absorbing species in the material or (b) an absorption cross-section (σ) and the density (N') of absorbers. For liquids, these relations are usually written as:

$$T = \frac{I}{I_0} = 10^{-\alpha l} = 10^{-\varepsilon l c} \quad (1)$$

Wherein $I_0$ is the intensity or power of the incident light and I is the intensity of the transmitted light.

Transmission (T) is expressed in terms of absorbance. For liquids, absorbance is defined as:

$$A = -\log_{10}\left(\frac{I}{I_0}\right) \quad (2)$$

From the above, it can be deduced that absorbance becomes linear with the concentration (or number density of absorbers) as shown by the following equation:

$$A = \varepsilon l c = \alpha l \quad (3)$$

According to the above equation, for a liquid, if the path length and the molar absorptivity or the absorption cross section are known, the concentration of a substance or the number density of absorbers can be calculated by measuring absorbance.

Typically, in analytical spectroscopy, a cuvette with a 1 cm path length is used in a standard system to simplify the above calculation. This allows the concentration of an unknown calculation to be deduced by measuring its absorbance and comparing it to a series of absorbance values of standard solutions shown in a standard curve.

However, in vertical spectrophotometry the path length varies from sample to sample. Further, the same problem may arise for very small volumes of sample in a horizontal system.

The present invention therefore seeks to allow an unknown path length to be determined by suing a high accuracy reference path length and certified reference solutions or material to achieve fully traceable measurements.

U.S. Pat. No. 5,959,738 (and its continuations—U.S. Pat. Nos. 6,188,476, 6,320,662, and 6,404,501) disclose a photometric method and a device for determining optical path lengths of liquid samples comprising analytes dissolved or suspended in a solvent by vertical spectrophotometry. This document also describes a method and apparatus for determining optical path length and sample concentration which provide accurate results. In this document, path length is calculated by measuring absorbance of the same sample at two different wavelengths and calculating the mathematical difference between the absorbance measure at the higher wavelength and the absorbance measurement at the lower wavelength and then dividing the obtained number by the mathematical difference between the absorbance measure at the higher wavelength and the absorbance measurement at the lower wavelength of a standard solution.

Although the methods and apparatus described in these documents are an improvement over other previous systems, the measurements are only comparative and are not suitable for working with the very small volumes required in biotechnology and pharmaceutical research.

WO2007/131945 discloses an apparatus having a source of electromagnetic radiation, a detector and a drop head comprising adapted to receive a drop of liquid and further adapted to be located, in use, in line with the source and the detector to allow analysis of the drop containing a sample. In this device the drop head is shaped to restrict the configuration of the drop so that surface tensions are more significant than gravity. This device is also an improvement over other prior art. However, it does not provide fully traceable results because each measurement cannot be validated to an accurate standard. Thus, the path length measurement obtained cannot be used as part of ISO-compliant protocols nor can it be used to obtain ISO-compliant results.

The present invention therefore seeks to provide a traceable method of determining an unknown optical path length.

DESCRIPTION OF THE INVENTION

According to the present invention there is provided a method for traceably determining an unknown optical path length of a sample in an optical measuring device, which optical measuring device is validated using a certified reference material having a specified nominal absorbance, the sample being dissolved or suspended in a solvent, which solvent is also the solvent of the certified reference material, wherein the certified reference material is contained in first and second closed cuvettes, which cuvettes have a first and second specified path length and a specified accuracy;

wherein absorbance of the certified reference material is measured to obtain a first absorbance measurement for the first specified path length; absorbance of the certified reference material is then measured for a second path length to obtain a second absorbance measurement;

wherein a dropping device drops a specified volume of the solvent on the optical measuring device so that the path length of the specified volume can be determined by reference to the first and second absorbance measurement;

wherein the dropper drops the sample on the optical measuring device, which sample has the same volume as the specified volume, thereby enabling a traceable absorbance measurement of the sample.

Preferably, the step of measuring absorbance of the certified reference material in the high accuracy cuvette comprises measuring absorbance at three predetermined wavelengths. More preferably, absorbance of the certified reference material in the high accuracy cuvette is measured at least two predetermined wavelengths. Even more preferably, absorbance of the certified reference material in the high accuracy cuvette is measured at three the predetermined wavelengths. In a preferred embodiment, the predetermined wavelengths are approximately 258 nm, 416 nm and 630 nm.

In a preferred embodiment, the high accuracy cuvette has a path length substantially in the range of 1 mm to 10 mm with a variation of up to 0.001 mm.

Preferably, the steps of measuring absorbance of the certified reference material, the solvent and the sample are performed at substantially negligible time intervals. More preferably the steps of measuring absorbance of the certified reference material, the solvent and the sample are performed simultaneously. Even more preferably, the step of measuring absorbance of the certified reference material and the sample are performed using the same optical path.

Preferably, the sample is delivered with a standard pipette. More preferably, accuracy of the pipette is measured by using the pipette to deliver a predetermined amount of the certified reference material, measuring absorbance of the predetermined amount and comparing absorbance of the predetermined amount with a predetermined absorbance value.

The above features allow the present method to be from two to three orders of magnitude more accurate than prior art devices. Further, the present invention makes possible to trace results to ISO standards; this is particularly useful in fields such as biotechnology in which sample volume can be very small thus making it very difficult to provide traceable measurements and results. Further, the present invention is cleaner and results obtained in this manner are less prone to contamination and background noise when compared with prior art devices. In addition, the invention provides an improvement in speed over prior art devices.

An exemplary embodiment will now be described in greater detail with reference to:

Figure 1:
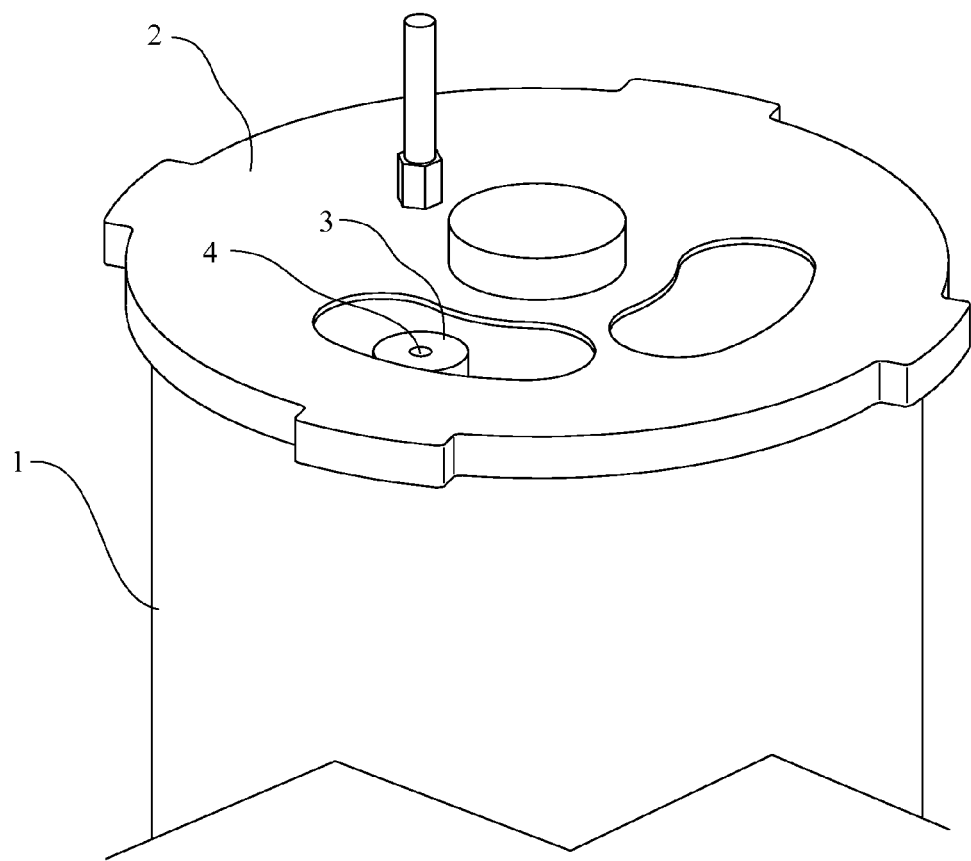
FIG. 1 shows a micro volume spectrophotometer.

FIG. 1 shows a micro volume spectrophotometer comprising a main housing 1 having a plinth 2 with an optical surface 3 adapted to receive a drop 4. In use, the housing can be rotated so that the drop is aligned with an optical fibre light source, which enables light to pass through the drop to a detector.

Figure 2:
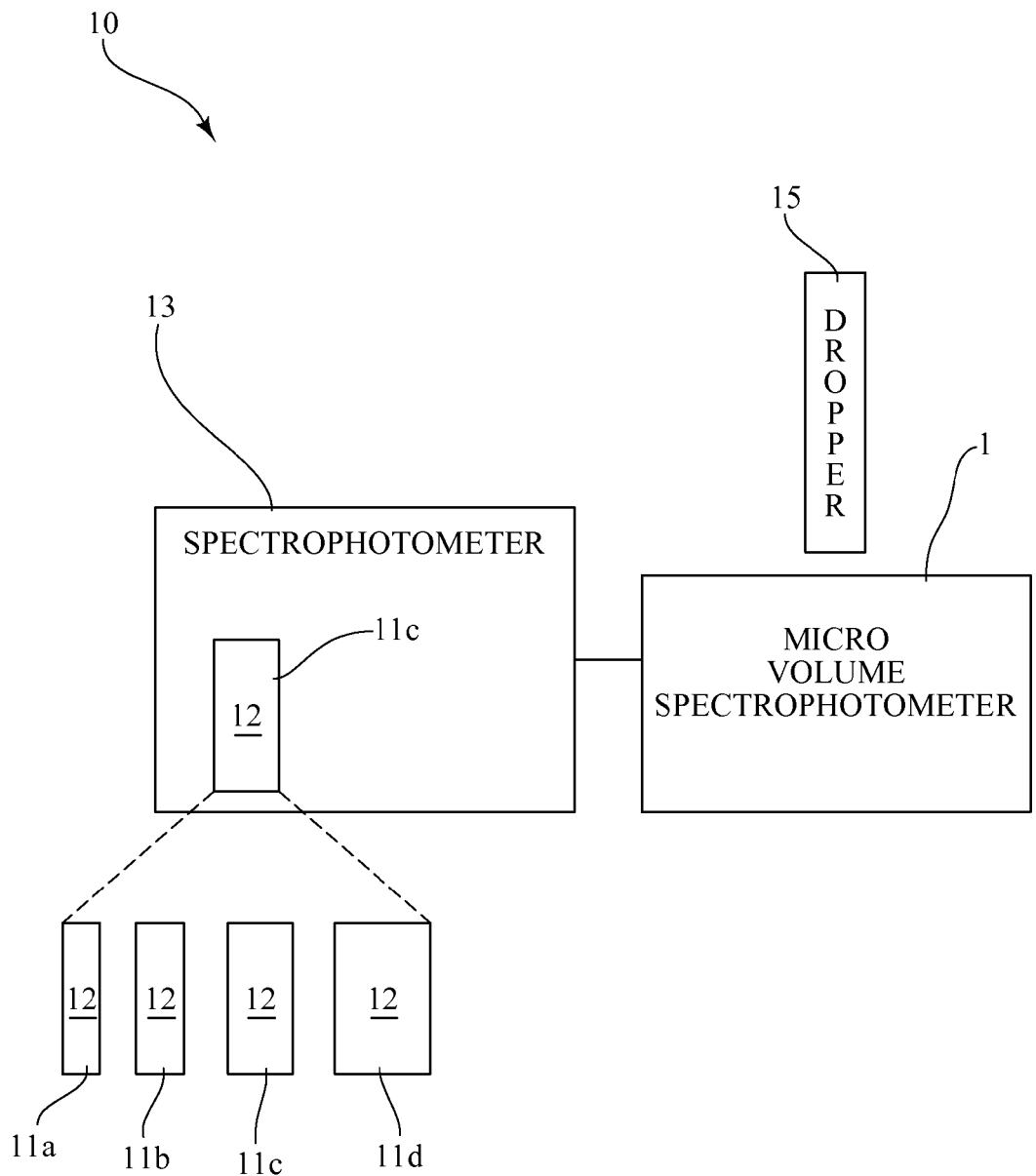
FIG. 2 is a schematic diagram of the system for determining path length in accordance with the present invention.

As shown in the schematic diagram of FIG. 2, the system for determining path length (or optical measuring device) includes a series of 1, 2, 5 and 10 mm path length closed high accuracy cuvettes or cells 11a, 11b, 11c, 11d having a tolerance of up to 0.001 mm. Secondly, the system includes a stable certified reference material (CRM) of nominal absorbance 1.000 absorbance units contained in the cuvettes 11a, 11b, 11c, 11d and having spectral characteristics allowing measurement values to be determined at three appropriate wavelength values.

For example, a commonly used reference is Starna Green™ material (which is manufactured and distributed by the assignee of the present application, Starna Scientific Limited of Essex, England) in which the wavelengths are nominally 258, 416 and 630 nm.

Modern spectrophotometers, such as the spectrophotometer 13 in FIG. 2, can be used to measure absorbance of a solution in the 0.1000 cm (1.000 mm) to 1.000 cm (10.000 mm) path length range. Devices such as the one described in WO2007/131945 can be used as part of a standard spectrophotometer set up or on their own. When this type of device is connected to a modern spectrophotometer, it is possible to measure absorbance of a sample in the device and a sample enclosed in a more conventional cuvette which can be located in the spectrophotometer or the additional device. In other words, the calibration relies on the ability of the spectrophotometer connected to the drop device which requires the optical path length to be determined, also being able to measure a conventional path length cuvette, in the range of 1 to 10 mm.

In this exemplary embodiment, the drop analyser (i.e., the micro volume spectrophotometer of FIGS. 1 and 2) is connected to a standard spectrophotometer (i.e., the spectrophotometer 13 of FIG. 2). In use, the present method eliminates all variables associated with lack of traceability with the exception of the pipette accuracy; however, pipette accuracy can be validated by measuring a predetermined volume of certified reference material, measuring absorbance thereof and comparing the measured absorbance value with a notional predetermined absorbance value for the volume targeted.

The spectrophotometer therefore need not take measurements under high accuracy conditions because the absorbance signals measured in the high accuracy cuvettes are adjusted in accordance with the ratio between the measurement and the absorbance of the unknown path length measurement. As a result, any fundamental instrumental errors are cancelled out, if negligible drift is assumed. Wavelength drift is defined as a variation in wavelength due to temperature variation of the light source. Consequently, the path length of any optical solution, drop, and meniscus between two parallel surfaces, in either a horizontal or vertical orientation can be determined.

In the plinth 2 shown in FIG. 1, the optical surface 3 has a diameter of 2 mm. If a drop 4 of a sample volume of 3 µl is placed on the optical surface 3 (e.g., via the dropper 15 shown in FIG. 2), the optical path length through the sample (or drop 4) is about 1 mm. It is then possible to compare the results with a normal 1 mm reference cell having a validated standard solution. The solvent should be the same in the sample and the standard solution.

In this embodiment, the measurements are performed through the same optical path; further, the measurements are performed substantially at the same time to minimise any drift in the system.

It should be apparent to a skilled man that other embodiments of the invention can be constructed. For example, different reference materials could be used. Further, whilst 1, 2, 5 and 10 mm path length cuvettes 11a, 11b, 11c, 11d have been described, a set could have any size in the range of 1 mm to 10 mm providing the cell dimensions do not have a variation higher than 0.001 mm for each predetermined size. Moreover, smaller 0.1 mm to 1.00 mm cells would theoretically work in the same manner.

In an alternative embodiment, a system could be custom-built using a different form of sample presentation. For example, a micro-plate reader having a cuvette reader position could be used instead of a standard spectrophotometer. A NanoDrop™ device or an equivalent could also be used.

In another alternative embodiment, the drop measuring device could be set up on its own or incorporated into a spectrophotometer system on manufacture; in that case, the surface could be used to measure absorbance of the reference material in the cell. Alternatively, the device may have a cuvette holder to allow the reference material in the cell to be analysed.

In yet another alternative embodiment, two different optical paths could be used to measure absorbance of the certified reference material and the unknown sample. However, this set up could experience more drift issues. Further, absorbance could be measured at intervals between measurements; however, these should be kept relatively small to minimise any relatively small drift component.

In contrast to the known methods of determining the path length of a drop, the solution of the invention is faster, less prone to contamination as no separate glass plates are required and achieves 2-3 orders more accurate results. The results are in addition absolute rather than comparative unlike the prior art examples.

The invention claimed is:

1. A method for traceably determining an unknown optical path length of a sample in an optical measuring device, which optical measuring device is validated using a certified reference material having a specified nominal absorbance, the sample being dissolved or suspended in a solvent, which solvent is also the solvent of the certified reference material, wherein the certified reference material is contained in first and second closed cuvettes, which cuvettes have a first and second specified path length and a specified accuracy, the method comprising the steps of:

measuring absorbance of the certified reference material to obtain a first absorbance measurement for the first specified path length;

measuring absorbance of the certified reference material for a second path length to obtain a second absorbance measurement;

using a dropper to drop a specified volume of the solvent on the optical measuring device so that the path length of the specified volume can be determined by reference to the first and second absorbance measurement; and using the dropper to drop the sample on the optical measuring device, which sample has the same volume as the specified volume, thereby enabling a traceable absorbance measurement of the sample.

2. The method according to claim 1, wherein the step of measuring absorbance of the certified reference material comprises measuring absorbance of the certified reference material at at least two predetermined wavelengths.

3. The method according to claim 2, wherein the step of measuring absorbance of the certified reference material consists of measuring absorbance of the certified reference material at three predetermined wavelengths.

4. The method according to claim 3, wherein the predetermined wavelengths are 258 nm, 416 nm and 630 nm.

5. The method according to claim 1, wherein the cuvette has a path length tolerance of 1/1000.

6. The method according to claim 1, wherein the certified reference material has a nominal absorbance of 1.000 absorbance units.

7. The method according to claim 1, wherein the steps of measuring absorbance of the certified reference material and measuring absorbance of the sample are performed substantially simultaneously.

8. The method according to claim 7, wherein the steps of measuring absorbance of the certified reference material and measuring absorbance of the sample are performed using the same optical path.

9. The method according to claim 1, further comprising the steps of: delivering the sample with a pipette; measuring accuracy of the pipette by using the pipette to deliver a predetermined amount of the certified reference material; measuring absorbance of the predetermined amount of certified reference material; and comparing the absorbance of the predetermined amount of certified reference material with a predetermined absorbance value.

* * * * *